(12) United States Patent
Jones, Jr. et al.

(10) Patent No.: US 9,090,925 B2
(45) Date of Patent: Jul. 28, 2015

(54) SYNTHESIS OF (6S)-5,6,7,8-TETRAHYDROFOLIC ACID

(75) Inventors: Gerald S. Jones, Jr., Norwood, MA (US); Joseph P. St. Laurent, Lakeville, MA (US); Scott A. Goodrich, Stoughton, MA (US); George Maguire, Newton, MA (US)

(73) Assignee: Chemic Laboratories Inc., Canton, MA (US)

( * ) Notice: Subject to any disclaimer, the term of this patent is extended or adjusted under 35 U.S.C. 154(b) by 0 days.

(21) Appl. No.: 13/523,431

(22) Filed: Jun. 14, 2012

(65) Prior Publication Data

US 2012/0315679 A1     Dec. 13, 2012

Related U.S. Application Data

(63) Continuation of application No. 12/592,770, filed on Dec. 2, 2009, now abandoned, which is a continuation of application No. 11/656,084, filed on Jan. 22, 2007, now abandoned.

(60) Provisional application No. 60/760,562, filed on Jan. 20, 2006.

(51) Int. Cl.
*C12P 17/18* (2006.01)
*C07D 475/04* (2006.01)

(52) U.S. Cl.
CPC ............ *C12P 17/182* (2013.01); *C07D 475/04* (2013.01)

(58) Field of Classification Search
CPC ......... C12P 17/12; C12P 17/14; C12P 17/165
See application file for complete search history.

(56) References Cited

U.S. PATENT DOCUMENTS

| | | | | |
|---|---|---|---|---|
| 4,929,551 A | * | 5/1990 | Eguchi et al. | 435/106 |
| 5,124,452 A | | 6/1992 | Gennari | |
| 5,350,850 A | * | 9/1994 | Vecchi | 544/258 |
| 5,710,271 A | * | 1/1998 | Felder et al. | 544/258 |

FOREIGN PATENT DOCUMENTS

WO  WO 03/018824  *  3/2003

OTHER PUBLICATIONS

Kuge et al., "Large-scale Chemoenzymic Synthesis of Calcium (6S)-5-Formyl-5,6,7,8-tetrahydrofolate [(−)-Lecucovorin] using the NADPH Recycling Method", J. Chem. Soc. Perkin Trans. 1 : 1427-1431 (1994).*
Futterman, "Enzymatic Reduction of Folic Acid and Dihydrofolic Acid to Tetrahydrofolic Acid", J. Biol. Chem. 228: 1031-8 (1957).*
Blair, et al., "A convenient method for the preparation of dl-5-methyltetrahydrofolic acid (dl-5-methyl-5,6,7,8-tetrahydropteroyl-L-monoglutamic acid)." Anal. Biochem 1970, 34, 376.
International Search Report for Application PCT/US2007/001574 dated Oct. 12, 2007.
Khalifa et al., "Über Pterinchemie 76. Mitteilung [1] Eine einfache Synthese von Leucovorin" Helv. Chim. Acta 63, 2554 (1980). (English abstract only).
Plante, et. al., "Enzyme studies with new analogs of folic acid and homofolic acid", J. Biol. Chem. vol. 242, No. 7, pp. 1466-1476; pp. 1468-1469 (1967).
Rees, et al., "Asymmetric reduction of dihydrofolate using dihydrofolate reductase and chiral boron-containing compounds" Tetrahedron 42, 117-136, 1986.
Temple, Jr. et al., "Preparation and Purification of L-(+)-5-Formyl-5,6,7,8,-tetrahydrofotic Acid", J. Med. Chem., vol. 22, No. 6, p. 731, 1979.

* cited by examiner

*Primary Examiner* — Jon P Weber
*Assistant Examiner* — Teresa E Knight
(74) *Attorney, Agent, or Firm* — Lando & Anastasi, LLP

(57) ABSTRACT

A process for the large-scale chemoenzymatic production of (6S)-5-methyl-5,6,7,8-tetrahydrofolic acid, also known as (6S)-5-methylTHFA, the process comprising the steps of: (1) reducing folic acid (FA) so as to yield dihydrofolic acid (DHFA); (2) stereoselectively reducing DHFA with dihydrofolate reductase (DHFR) in the presence of NADP/NADPH, glucose and GluDH so as to yield (6S)-THFA; (3) converting (6S)-THFA to (6S)-5-methlTHFA; and (4) isolating (6S)-5-methylTHFA.

14 Claims, 4 Drawing Sheets

US 9,090,925 B2

SYNTHESIS OF (6S)-5,6,7,8-TETRAHYDROFOLIC ACID

REFERENCE TO PENDING PRIOR PATENT APPLICATION

This patent application is a continuation of pending prior U.S. patent application Ser. No. 12/592,770, filed Dec. 2, 2009 which claims priority to U.S. patent application Ser. No. 11/656,084, filed Jan. 22, 2007 by Gerald S. Jones, Jr. et al. for SYNTHESIS OF (6S)-5-METHYL-5,6,7,8-TETRAHYDROFOLIC ACID, which in turn claims benefit of prior U.S. Provisional Patent Application Ser. No. 60/760,562, filed Jan. 20, 2006 by Gerald S. Jones, Jr. for (6S)-5-METHYL-5,6,7,8-TETRAHYDROFOLIC ACID.

The above-identified patent applications are hereby incorporated herein by reference.

FIELD OF THE INVENTION

This invention relates to the chemical synthesis of tetrahydrofolic acid in general, and more particularly to a method for the large-scale chemoenzymatic production of (6S)-5-methyl-5,6,7,8-tetrahydrofolic acid, also sometimes referred to as (6S)-5-methylTHFA.

BACKGROUND OF THE INVENTION

Folic acid (FA), also known as pteroyl-L-glutamic acid, is a vital co-factor in enzymatic reactions necessary for the synthesis of nucleic acids, amino acids, and other biological molecules. The structure of folic acid is shown in FIG. 1, and again in FIG. 2 where n=1. Although many organisms are capable of synthesizing folic acid, humans are unable to synthesize folic acid, and must depend on adequate dietary intake of this essential nutrient.

Without adequate intake of folic acid, humans may develop a folate deficiency. Folate deficiency has several negative impacts on the human body, including but not limited to: (i) the defective maturation of different cell types; (ii) nervous system disorders; (iii) a decreased immune response; and (iv) the development of peripheral vascular disease. It has also been found that insufficient folate levels during pregnancy correlate with the occurrence of neural tube defects in newborns. Low folate levels may also lead to megaloblastic anemia, a disorder which results in inadequate production of red blood cells, particularly during pregnancy and in geriatrics.

The clear connection between adequate folate intake and health has resulted in the establishment of a recommended dietary allowance (RDA) for folic acid by the U.S. government. Although folic acid is currently added to all commercial over-the-counter (OTC) vitamin preparations, and to some foods, folic acid is not the primary form of folate which is found naturally in fresh foods. More commonly, the primary forms of folate which are found in natural fresh foods are polyglutamates (e.g., the structure shown in FIG. 2 where n=6). Of these polyglutamates, the polyglutamate forms of (6S)-5-methylTHFA (the structure shown in FIG. 3 where R=CH$_3$) and (6S)-5-formylTHFA (the structure shown in FIG. 3 where R=CHO) predominate. However, since the primary form of folate which can be absorbed by the human body bears only a single glutamic acid residue, polyglutamates, after ingestion, must be processed enzymatically in the digestive tract prior to absorption. Another difference between folic acid and natural folates (e.g., polyglutamates) is that the folates in fresh, uncooked foods are usually present as a reduced form. One example of a reduced folate is tetrahydrofolic acid (THFA) and its derivatives.

There is reason to believe that in a segment of the population, the absorption of reduced folates, such as tetrahydrofolic acid (THFA), may exceed that of folic acid, resulting in greater bioavailability. Thus, dietary supplementation with these reduced folates (e.g., THFA) may constitute an improved method for meeting the RDA of folic acid. In fact, the calcium salt of (6S)-5-methylfolate (FIG. 4), also known as, L-methylfolate, is currently commercially available under the trade name Metafolin™ for use as a dietary supplement. In addition to the foregoing, (6S)-5-methylfolate may be the body's preferred form of folate, since it is the predominant form of folate found in humans.

Although the importance of folic acid in the diet has been recognized, prior and widespread use of reduced folates as dietary supplements has been limited, in part by the stereochemistry of these compounds. The chemical structure of folic acid contains a single chiral center in the glutamic acid portion of the molecule (see FIG. 1, where the chiral center is denoted by an asterisk). Reduction of folic acid to THFA creates a second chiral center at the 6-position (the sixth carbon atom) of the pteridine nucleus. When the reduction of folic acid is carried out chemically, a mixture of two isomers called diastereomers (or more appropriately, epimers) results, whereby the orientation of substituents at the 6-position in each isomer is different. Each of these distinct orientations, or configurations, is designated as either S or R in accordance with the Cahn-Ingold-Prelog convention. As a result of the aforementioned reduction of folic acid, one-half of the molecules have the S-configuration at the 6-position, and one-half of the molecules have the R-configuration at the 6-position. Conversely, reduction of folic acid enzymatically, e.g., by the enzyme dihydrofolate reductase (DHFR), proceeds stereoselectively, and results in only the production of (6S)-THFA (see FIG. 5). It is important to note that all tetrahydrofolates that occur naturally are found in only one diastereomeric form, i.e., the absolute configuration at the 6-position is either S or R. Accordingly, the S designation is assigned to (i) naturally-occurring THFA, (ii) 5-methylTHFA, and (iii) 5-formylTHFA, whereas the R designation is assigned to (i) naturally-occurring 5,10-methyleneTHFA, and (ii) 10-formylTHFA.

In addition to the naturally-occuring diastereomeric forms of reduced folates, it has been found that some unnatural isomers of reduced folates (i.e., those in which the configuration at the 6-position is opposite that of natural isomers) can exhibit considerable absorption in the human gastrointestinal (GI) tract. However, a low order of biological activity has been ascribed to the unnatural isomers and, more importantly, it appears that the unnatural isomers may have an inhibitory effect upon certain enzymatic processes. Due to these factors, and because the effect of chronic or long-term exposure to these unnatural isomers is unknown, there has been a recent trend to use only diastereomerically pure (or natural) (6S)-isomers of reduced folates as therapeutic agents, e.g., (6S)-5-formylTHFA or calcium leucovorin, and dietary supplements (e.g., Metafolin™)

A variety of methods are currently available for the production of these desirable pure folate isomers. At present, the methods which are used for commercial production of folate isomers rely on the resolution of pairs of diastereomers, particularly by fractional crystallization/recrystallization techniques. For example, Metafolin™ is produced by such a method. Some of these methods produce large volumes of undesirable by-products which need to be removed, and thus negatively influence the economy and efficiency of the process. Others of these methods require multiple fractionations/recrystallizations to achieve a product of high diastereomeric excess, and therefore can be time-consuming and costly.

In addition to the foregoing, there is an approach which uses the chromatographic separation of diastereomers, but it does not lend itself to large-scale production of pure folate isomers. Furthermore, there is a method which synthesizes (6S)-THFA via the stereoselective catalytic hydrogenation of dihydrofolic acid (DHFA), but the cost of the exotic organometallic catalyst(s) is prohibitive for large-scale production. A chemoenzymatic method has also been described for producing small quantities of (6S)-THFA and derivatives, but this latter method is typically regarded as unsuitable for commercial application due to its complexity (*Tetrahedron* 1986, 42, 117-136).

Thus, the foregoing approaches do not provide a cost-effective, large-scale method to produce the pure reduced folates (e.g., (6S)-THFA).

An enzymatic process for the production (6S)-THFA, which involves the reduction of DHFA with DHFR in the presence of NADPH, glucose, and glucose dehydrogenase (GluDH), is disclosed in U.S. Pat. No. 4,929,551 to Eguchi for PROCESS FOR PRODUCING L(−)-TETRAHYDROFOLIC ACID. In this method, glucose/GluDH functions as an NADPH-regenerating system, allowing for an efficient, cost-effective process. Thus, diastereomerically pure THFA was produced from 100 mL of an aqueous solution containing 52 mM DHFA, 61 mM glucose, 1.0 mM NADPH, 5.7 U/mL DHFR and 5.6 U/mL GluDH. Due to its intrinsic instability, the (6S)-THFA produced was isolated as its $N^5,N^{10}$-methylylidene derivative (FIG. 6; 2.43 g). In accordance with the patent, the $N^5,N^{10}$-methylylidene derivative (FIG. 6; 2.43 g) was then converted to calcium leucovorin (L-formylfolate).

However, there has been recent interest in using L-methylfolate, rather than L-formylfolate, as the pure reduced folate isomer for a dietary supplement. While the aforementioned enzymatic process of U.S. Pat. No. 4,929,551 is adequate to produce L-formylfolate, it is not adequate to produce L-methylfolate.

Accordingly, there is still a need to provide a cost-effective, large-scale method to produce L-methylfolate.

SUMMARY OF THE INVENTION

The present invention provides a process for the large-scale chemoenzymatic production of (6S)-5-methyl-5,6,7,8-tetrahydrofolic acid, also known as (6S)-5-methylTHFA.

In one preferred form of the invention, the process comprises the steps of:

(1) reducing commercially available folic acid (FA) with zinc powder under basic conditions to yield dihydrofolic acid (DHFA);

(2) stereoselectively reducing DHFA with dihydrofolate reductase (DHFR) in the presence of an NADP/NADPH recycling system, glucose and GluDH so as to yield (6S)-THFA;

(3) converting (6S)-THFA to (6S)-5-methylTHFA in situ by conventional methods; and (4) isolating (6S)-5-methylTHFA as its calcium salt.

In another form of the invention, there is provided a chemoenzymatic process for producing calcium (6S)-5-methylTHFA, comprising the steps of:

allowing DHFR to act upon DHFA in the presence of NADP, NADPH glucose and GluDH;

accumulating (6S)-THFA in aqueous solution and converting it in situ to (6S)-5-methylTHFA; and recovering (6S)-5-methylTHFA as its calcium salt therefrom.

In another form of the invention, there is provided a process for the large-scale chemoenzymatic production of (6S)-5-methyl-5,6,7,8-tetrahydrofolic acid, also known as (6S)-5-methylTHFA, the process comprising the steps of:

(1) reducing folic acid (FA) so as to yield dihydrofolic acid (DHFA);

(2) stereoselectively reducing DHFA with dihydrofolate reductase (DHFR) in the presence of NADP/NADPH, glucose and GluDH so as to yield (6S)-THFA;

(3) converting (6S)-THFA to (6S)-5-methylTHFA; and (4) isolating (6S)-5-methylTHFA.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENT

First Embodiment

Figure 1:
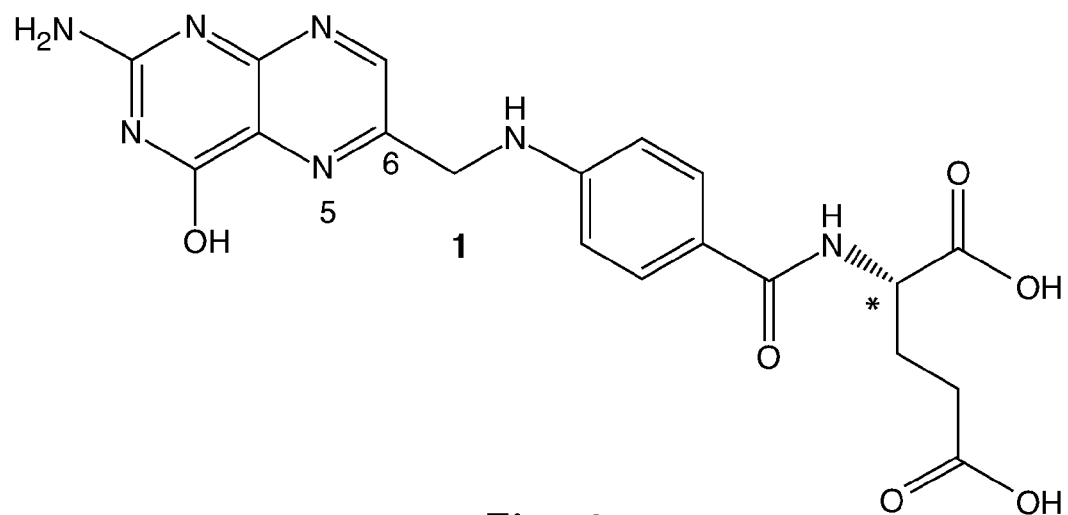
FIG. 1 shows the chemical structure of folic acid.
Figure 2:
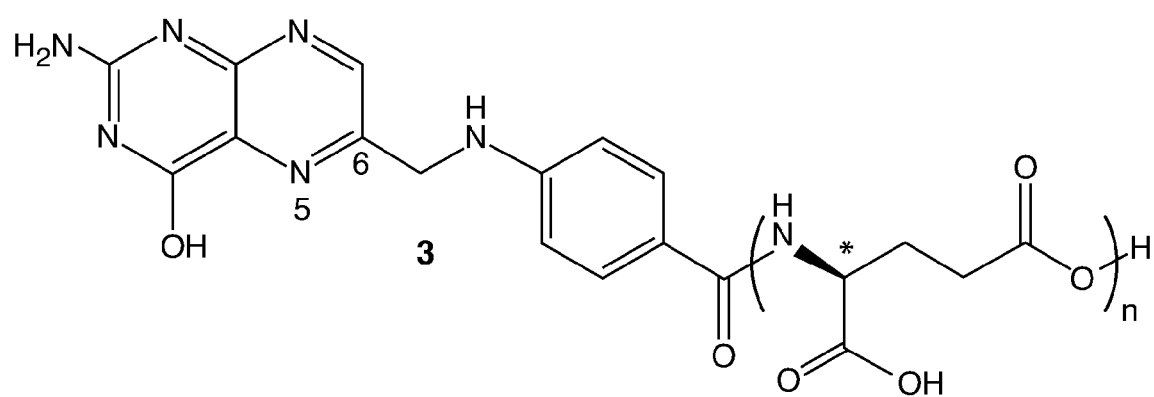
FIG. 2 is another representation of the stereoisomer of folic acid (n=1) shown in FIG. 1.
Figure 3:
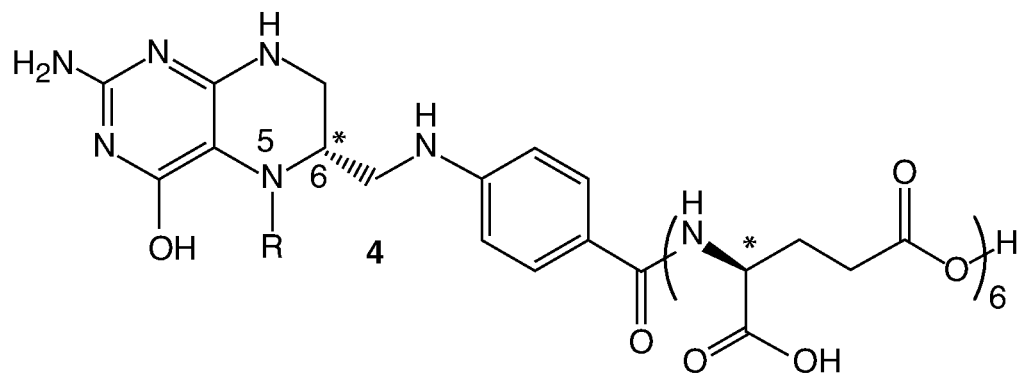
FIG. 3 is the general structure for the polyglutamate form of isomerically pure reduced folates.
Figure 4:
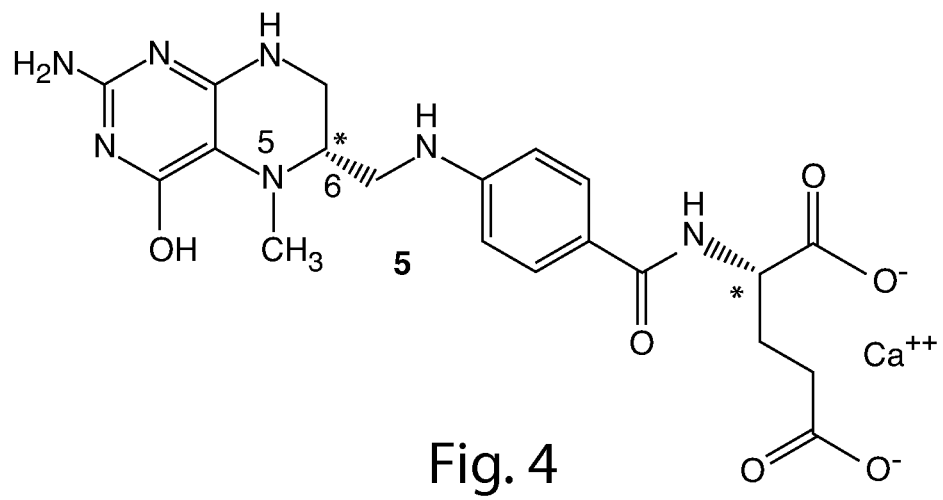
FIG. 4 shows the chemical structure of (6S)-5-methylfolate, calcium salt.
Figure 5:
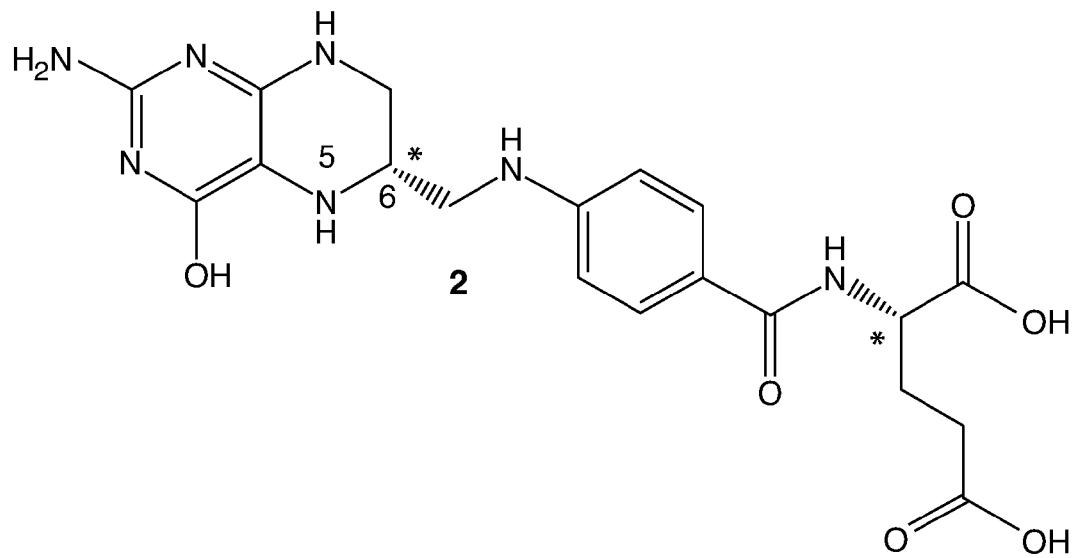
FIG. 5 is the chemical structure of naturally occurring (6S)-tetrahydrofolic acid.
Figure 6:
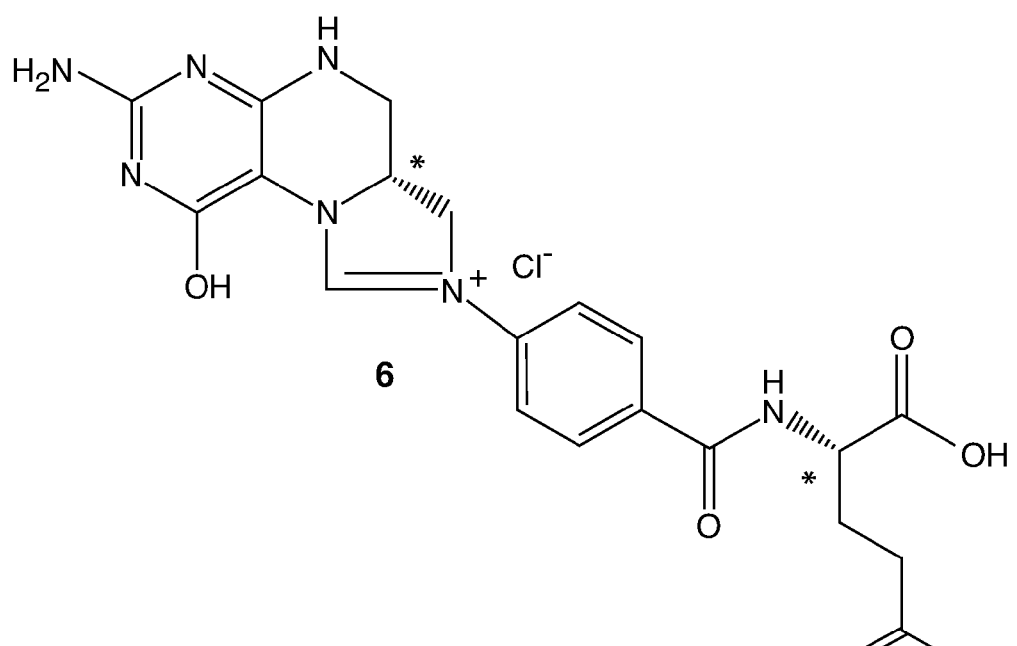
FIG. 6 shows the chemical structure for $N^5,N^{10}$-methylylidene.

In one preferred embodiment of the present invention, there is provided a one-pot process for the large-scale chemoenzymatic production of (6S)-5-methyl-5,6,7,8-tetrahydrofolic acid, also known as (6S)-5-methylTHFA. In this preferred form of the invention, the process comprises the steps of:

(1) reduction of commercially available folic acid (FA) with zinc powder under basic conditions to give dihydrofolic acid (DHFA);

(2) stereoselective reduction of DHFA with dihydrofolate reductase (DHFR) in the presence of NADP and an NADPH recycling system, i.e., glucose/GluDH, to give (6S)-THFA;

(3) in situ conversion of (6S)-THFA to (6S)-5-methylTHFA by conventional methods; and (4) isolation of (6S)-5-methylTHFA as its calcium salt. More particularly, in the first step, in an appropriately-sized reaction vessel, commercially-available FA is reduced to DHFA by stirring a basic solution (e.g., pH 13.5) of FA, sodium hydroxide (NaOH), and zinc powder for approximately two hours at 40° C. under $N_2$. This is further described in *J. Chem. Soc, Perkin Trans.* 1 1994, 1427. The pH of the reaction mixture is then adjusted with phosphoric acid ($H_3PO_4$) which allows isolation of zinc phosphate and excess zinc powder by filtration ($N_2$). The filtrate (pH 7.5) is returned to the reaction vessel. It is important to note that due to the propensity of the reduced folates to oxidize, all reactions and procedures in this process are performed under an inert atmosphere, e.g., $N_2$ or Argon.

There are other methods currently available for the chemical reduction of FA. Additional literature examples may be found in Temple, Jr. et al., "Preparation and Purification of L-(±)-5-Formyl-5,6,7,8,-tetrahydrofolic Acid", *J. Med. Chem.* 1979, volume 22, number 6, page 731 and *Helv. Chim. Acta* 1980, 63, 2554. However, these methods could result in the accumulation of a mixture of THFA diastereomers, which would lower the diastereomeric purity of the target compound.

After FA is reduced to DHFA, the DHFA must then be converted to (6S)-THFA. More particularly, in the second step of the process, while maintaining a nitrogen atmosphere, a series of reactants are added to the reaction vessel. By way of example but not limitation, the following quantities of reactants are added: glucose (4.5 kg, 25.0 mol), glucose dehydrogenase (GIuDH) (1,500,000 U), dihydrofolate reductase (DHFR) (750,000 U), and NADP (86.7 g, 0.21 mol). The mixture is stirred at 40° C. for two hours, or until such a time that the conversion of DHFA to (6S)-THFA is complete. The reaction mixture is then filtered, and the filtrate is returned to the reaction vessel. The enzymes used in this process can be of various forms and from various sources (e.g., GluDH, DHFR). In a preferred embodiment, each enzyme is immobilized on a non-reactive support, which would allow easy isolation and/or recovery of the enzymes, and potential reuse.

In accordance with the third step of the present invention, wherein the (6S)-THFA is converted to the corresponding 5-methyl derivative, sodium ascorbate (1 mol %) is added to the reaction vessel, the pH is adjusted to 9, and the reaction mixture is cooled to <10° C. (6S)-THFA is converted to the corresponding 5-methyl derivative by first adding an appropriate amount of formaldehyde (3 molar excess, based on the substrate) at a rate such that the internal temperature is maintained at <30° C. At an internal temperature of 5° C., a suspension of sodium borohydride ($NaBH_4$) (4.5 molar excess, based on the substrate) in NaOH solution is then added at a rate such that the internal temperature is maintained at <20° C. After the addition of the NaOH solution is completed, the reaction mixture is slowly brought to 60° C. and maintained there for 15 minutes. The reaction mixture is then cooled to <5° C., and the pH is adjusted to approximately 7.1 by the addition of 37% hydrochloric acid (HCl). The precipitate of inorganic salts is removed by filtration, and the filtrate is returned to the reaction vessel.

An alternative method for the synthesis of (6R)-5-methylTHFA is described in *Anal. Biochem.* 1970, 34, 376.

Another alternative method for synthesizing (6S)-5-methylTHFA is by the sequential treatment of the (6S)-THFA solution with 36% formic acid ($HCO_2H$), followed by $NaBH_4$ (sodium borohydride, or sodium tetrahydroborate).

In the fourth step of the present invention, $CaCl_2$ solution is added to the final filtrate contained in the reaction vessel, and the pH is adjusted to 7.0. The internal temperature is maintained at 10° C. to allow the product, i.e., calcium 5-methylTHFA, to crystallize.

Second Embodiment

The following process may also be used for the large-scale chemoenzymatic production of (6S)-5-methyl-5,6,7,8-tetrahydrofolic acid, also known as (6S)-5-methylTHFA. Accordingly, in another preferred embodiment, there is described a one-pot process for the large-scale chemoenzymatic production of (6S)-5-methyl-5,6,7,8-tetrahydrofolic acid (or 5-MeTHFA), which comprises the following four discrete steps:

(1) reduction of commercially available folic acid (FA) with zinc powder under basic conditions to give dihydrofolic acid (DHFA);

(2) stereoselective reduction of DHFA with dihydrofolate reductase (DHFR) in the presence of NADP and an NADPH recycling system, i.e., glucose/glucose dehydrogenase (GluDH), to yield (6S)-THFA;

(3) in situ conversion of (6S)-THFA to (6S)-5-methylTHFA by conventional methods; and (4) isolation of (6S)-5-methylTHFA as its calcium salt.

Figure 7:
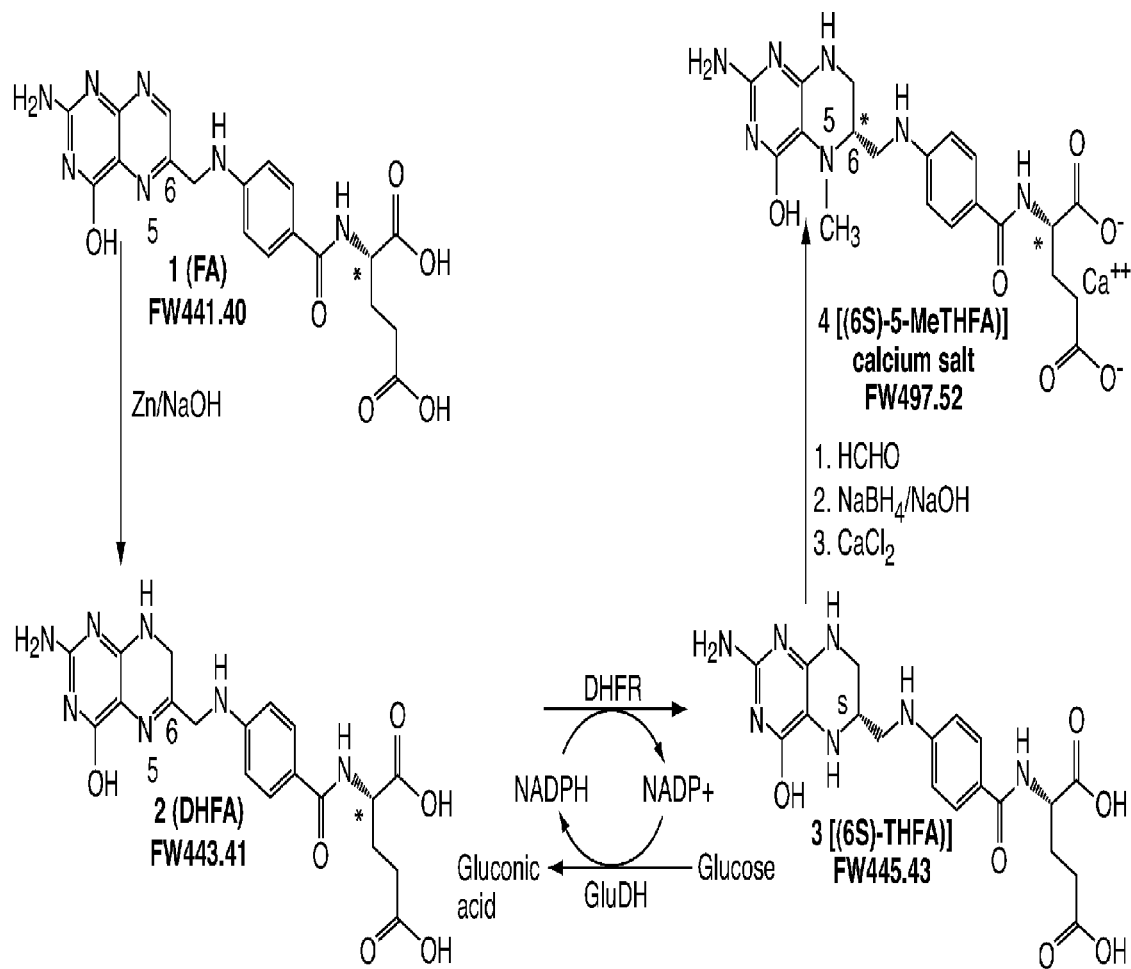
FIG. 7 is a schematic drawing showing an illustrative process of the present invention.

The process of the second embodiment of the present invention is illustrated in FIG. 7.

More particularly, in the first step, commercially-available FA is weighed into an appropriately-sized reaction vessel, and IN NaOH (approximately 7 mL/g) is added. The vessel is fitted with a stirrer, an $N_2$ inlet, and a pH electrode, and is then heated to 40-45° C. When the dissolution of FA is complete, the pH is adjusted to approximately 13.5 with 10N NaOH, and zinc powder (approximately 5.3 molar equivalents) is added. The mixture is stirred under $N_2$ for a period of between 2-4 hours. The pH is adjusted to approximately 7.5 by the addition of phosphoric acid ($H_3PO_4$), and the mixture is filtered under $N_2$ to remove zinc phosphate and any unreacted zinc powder. The filtrate is diluted with water (2-8 volumes) and returned to the reaction vessel. At this point, the vessel contains the DHFA solution. It is important to note that due to the propensity of the reduced folates to oxidize, all reactions and procedures in this process are performed under an inert atmosphere, i.e., $N_2$ or Argon.

The solution containing DHFA must then be converted to (6S)-THFA. More particularly, and in the second step of the process, the following reactants are added in succession to an appropriately sized vessel: glucose (approximately 1.2 molar equivalents), GluDH (approximately 60 U/mmole glucose) and DHFR (approximately 35 U/mmole substrate). Then 0.05M phosphate buffer (pH approximately 7.5; one volume) is added, and the resultant solution is added to the DHFA solution in one portion. The pH is adjusted to approximately 7.5, as needed, and NADP (0.01 molar equivalent) is added. The mixture is stirred at 22-30° C. for 2 hours, or until such a time that the conversion of DHFA to (6S)-THFA is complete, as determined by high performance liquid chromatography (HPLC). The pH is maintained at between 7.40-7.50 during the reaction period by the addition of 1N NaOH, as needed. The flask is fitted with a thermometer and transferred to a cooling bath, so that the internal temperature does not exceed 10° C.

In accordance with the third step of the present invention, wherein the (6S)-THFA is converted to the corresponding 5-methyl derivative, the pH is adjusted to approximately 9.0 by the addition of 10N NaOH, and formaldehyde (approximately 3 molar equivalents) is added at a rate such that the internal temperature is maintained at <20° C. When the internal temperature has equilibrated and does not exceed 10° C., a suspension of sodium borohydride ($NaBH_4$) (4.5 molar excess, based on the substrate) in 0.2N NaOH solution is added at a rate such that the internal temperature is maintained at <20° C. After the addition is completed, the reaction mixture is slowly heated to 60° C. and maintained there for 15 minutes. The reaction is monitored by HPLC. The reaction mixture is cooled to <10° C., and the pH is adjusted to approximately 7.1 by the careful addition of 37% HCl. The flask is stored under $N_2$ at 0±5° C. for a period of between 2-24 hours, whereupon precipitated inorganic salts are removed by filtration. The filtrate is returned to the reaction vessel, and pH is adjusted to approximately 7.0, as needed.

In the fourth step of the process of the present invention, 2-4M $CaCl_2$ solution (1.5-2 molar equivalents $CaCl_2$) is added to filtrate in the vessel, and the pH is adjusted to 7.0. The flask is stored under $N_2$ at 0±5° C. for a period sufficient to allow the product, calcium 5-methylTHFA, to crystallize. The product is collected by vacuum filtration, washed with copious amounts of cold water, dried under vacuum, and stored under $N_2$.

It should be appreciated that with the present invention, one or more of the aforementioned steps 1 through 4 may be varied without departing from the scope of the present invention.

In one such alternative approach, the first step of the aforementioned process, i.e., wherein FA is reduced to DHFA, may be substituted with a process utilizing two solutions. More particularly, in this alternative approach, a first solution is made by weighing commercially-available FA into an appropriately-sized reaction vessel fitted with a stirrer, an $N_2$ inlet, and a pH electrode. Water is added, and to the resulting stirred suspension, NaOH solution is then added (~2 molar equivalents). This solution is then diluted, as necessary, with additional water (i.e., total water=10-500 mL/g FA) and will be used in a subsequent step.

Subsequently, a second solution is made by weighing ascorbic acid (AA; 2-70 molar equivalents) into a separate appropriately-sized reaction vessel fitted with a stirrer and a pH electrode. Water is added (5-50 mL/g AA), and the pH of the resultant solution is adjusted to 6 with NaOH solution. This second solution is added to the first solution, and while stirring under $N_2$ at ambient temperature (e.g., 50° C.), sodium dithionite (1.5-30 molar equivalents) is added. Stirring is continued until essentially all of the FA has been converted to DHFA, as determined by appropriate analytical method(s).

The following two tables illustrate various amounts of reactants which may be used to create the two solutions necessary to reduce FA to DHFA in the preceding process:

| Example 1 (T = ambient). | wt, g | FW | moles | equiv | [ ], M |
|---|---|---|---|---|---|
| folic acid | 0.0382 | 441.4 | 0.00009 | | 0.009 |
| water (mL) | 1.6 | | | | |
| NaOH (as 0.1N NaOH) | 0.0064 | 40.00 | 0.00016 | 36.5 | 0.316 |
| ascorbic acid | 1.000 | 176.12 | 0.006 | 65.6 | 0.568 |
| water (mL) | 5 | | | | |
| 1N NaOH (µL) | 3000 | | 0.0030 | | |
| $Na_2S_2O_4$ | 0.400 | 174.11 | 0.002 | 26.5 | |
| NaOH (total) | | | 0.00316 | | |
| total volume (mL) | 10 | | | | |

| Example 2 (T = 40° C.). | wt, g | FW | moles | equiv | [ ], M |
|---|---|---|---|---|---|
| folic acid | 2.21 | 441.4 | 0.00501 | | 0.138 |
| water (mL) | 24 | | | | |
| 10N NaOH (µL) | 1000 | 40.00 | 0.01000 | 2.3 | 0.311 |
| ascorbic acid | 2.23 | 176.12 | 0.0127 | 2.5 | 0.349 |
| water (mL) | 10 | | | | |
| 10N NaOH (µL) | 1300 | | 0.0013 | | |
| 1N NaOH (µL) | | | 0.0000 | | |
| $Na_2S_2O_4$ | 4.39 | 174.11 | 0.0252 | 5.0 | 0.695 |
| NaOH (total) | | | 0.01130 | | |
| total volume (mL) | 36.30 | | | | |

Third Embodiment

The following process may also be used for the large-scale chemoenzymatic production of (6S)-5-methyl-5,6,7,8-tetrahydrofolic acid, also known as (6S)-5-methylTHFA.

Accordingly, in the first step, folic acid (FA) (10 g) is suspended in water (50 mL) and concentrated ammonium hydroxide (3.2 mL) is added to dissolve the solid and attain a pH of 8.1. To this, a solution having a pH of 8 and containing ascorbic acid (10 g), concentrated ammonium hydroxide (4.9 mL) and water (50 mL) is then added. The pH of the resulting solution is approximately 8. This solution is then stirred under $N_2$ and heated to a temperature of 60° C. To this mixture is added sodium dithionite (20 g). The pH of the resulting solution is 5.9. This solution is allowed to stir under $N_2$, at 60° C. for 30 minutes. The pH is adjusted to 3 by the addition of concentrated hydrochloric acid (13.5 mL). To this mixture is added methanol (400 mL). This mixture is allowed to stir for 15 minutes, and the solid precipitate is recovered by vacuum filtration.

In the second step, the recovered solid is suspended in water (100 mL) and concentrated ammonium hydroxide (7.2 mL) is added to dissolve the solid and attain a pH of 8.6. The pH of this solution is adjusted to 7.5 by the addition of 6N hydrochloric acid (9 mL). To this solution is added glucose dehydrogenase (20 mg), dihydrofolate reductase (7 mg), NADP (280 mg), glucose (6 g) and water (40 mL). This solution is allowed to stir under $N_2$ for 1 hour. After this time glucose dehydrogenase (16 mg), dihydrofolate reductase (8 mg) and water (20 mL) is added. This solution is allowed to stir for 3.5 hours. The pH of this solution is maintained at 7.5 by the intermittent addition of concentrated ammonium hydroxide. Concentrated hydrochloric acid (9.5 mL) is added to the solution in order to attain a pH of 2.9. The precipitate formed is isolated by centrifugation or other suitable means. The solid is suspended in water (100 mL) and isolated by vacuum filtration. The solid is dried in vacuo at 40° C. overnight to give 5.037 grams of crude tetrahydrofolic acid.

In the third step, the solid, or crude, tetrahydrofolic acid is suspended in water (40 mL) and allowed to stir under $N_2$ and concentrated ammonium hydroxide (2.5 mL) is added to dissolve the solid and attain a pH of 9. Next, 37% aqueous formaldehyde (2 mL) is added to this solution, and allowed to stir for 5 minutes. A solution containing sodium borohydride (1.5g), water (6 mL) and concentrated ammonium hydroxide (0.5 mL) is then added. This solution is allowed to stir for 30 minutes.

In the fourth step, a solution containing calcium chloride dihydrate (2.3 g) in methanol (100 mL) is added to the resulting solution of the third step. The precipitate formed was isolated by vacuum filtration, dried in vacuo at 40° C. overnight to provide 5.3 grams of crude calcium 6-methyl tetrahydrofolate.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:
1. A process for the large-scale chemoenzymatic production of (6S)-5-methyl-5,6,7,8-tetrahydrofolic acid, also known as (6S)-5-methylTHFA, the process comprising the steps of:
   (1) reducing folic acid (FA) with zinc powder under basic conditions to yield dihydrofolic acid (DHFA);

(2) stereoselectively reducing DHFA with dihydrofolate reductase (DHFR) in the presence of an NADP/NADPH recycling system, glucose and GluDH so as to yield (6S)-THFA;

(3) converting (6S)-THFA to (6S)-5-methylTHFA in situ by conventional methods; and (4) isolating (6S)-5-methylTHFA as its calcium salt;

wherein (6S)-5-methyl-THFA is produced without isolation of an intermediate.

2. A chemoenzymatic process for producing calcium (6S)-5-methylTHFA, comprising the steps of:

(1) allowing dihydrofolate reductase (DHFR) to act upon dihydrofolic acid (DHFA) in the presence of NADP, NADPH glucose and GluDH;

(2) accumulating (6S)-THFA in aqueous solution and converting it in situ to (6S)-5-methylTHFA; and (3) recovering (6S)-5-methylTHFA as its calcium salt therefrom;

wherein (6S)-5-methyl-THFA is produced without isolation of an intermediate.

3. A process for the large-scale chemoenzymatic production of (6S)-5-methyl-5,6,7,8-tetrahydrofolic acid, also known as (6S)-5-methylTHFA, the process comprising the steps of:

(1) reducing folic acid (FA) so as to yield dihydrofolic acid (DHFA);

(2) stereoselectively reducing DHFA with dihydrofolate reductase (DHFR) in the presence of NADP/NADPH, glucose and GluDH so as to yield (6S)-THFA;

(3) converting (6S)-THFA to (6S)-5-methylTHFA; and (4) isolating (6S)-5-methylTHFA;

wherein (6S)-5-methyl-THFA is produced without isolation of an intermediate.

4. The process according to claim 3 wherein step 1 further comprises stirring a solution of FA, NaOH and zinc powder for approximately two hours at approximately 40° C.

5. The process according to claim 3 wherein at least one step of the process is performed in an inert atmosphere.

6. The process according to claim 5 wherein the inert atmosphere comprises $N_2$.

7. The process according to claim 5 wherein the inert atmosphere comprises Ar.

8. The process according to claim 3 wherein step 1 further comprises:

(i) suspending folic acid in water and adding an NaOH solution so as to create a first solution;

(ii) creating a solution of ascorbic acid and water and adding an NaOH solution so as to create a second solution; and (iii) combining the second solution and the first solution, adding sodium dithionite and stirring until the folic acid has been converted to DHFA.

9. The process according to claim 3 wherein step 2 further comprises stirring the DHFA, glucose, GluDH, DHFR and NADP/NADPH for 2 hours at 40° C.

10. The process according to claim 3 wherein step 2 further comprises stirring the DHFA, glucose, GluDH, DHFR and NADP/NADPH for 2 hours at a temperature between 22° C. –30° C.

11. The process according to claim 3 wherein step 2 further comprises:

(i) stirring the DHFA, glucose, GluDH, DHFR, NADP/NADPH and water for 1 hour; and (ii) adding additional amounts of GluDH, DHFR and water and stirring for approximately 3.5 hours.

12. The process according to claim 3 wherein step 3 comprises adding a suspension of $NaBH_4$ in NaOH.

13. The process according to claim 3 wherein step 4 comprises adding a solution containing $CaCl_2$.

14. The process according to claim 3 wherein step 4 comprises adding a solution containing calcium chloride dihydrate in methanol.

* * * * *